United States Patent [19]

Kanamoto et al.

[11] 4,274,415
[45] Jun. 23, 1981

[54] SURGICAL CLIP AND ITS ASSEMBLY

[75] Inventors: Sakumi Kanamoto, Mukoshi; Akio Ishida, Kameokashi, both of Japan

[73] Assignee: Maruho Co., Ltd., Osaka, Japan

[21] Appl. No.: 5,867

[22] Filed: Jan. 23, 1979

Related U.S. Application Data

[63] Continuation-in-part of Ser. No. 765,742, Feb. 4, 1977, abandoned.

[30] Foreign Application Priority Data

| Jul. 16, 1976 | [JP] | Japan | 51-95530 |
| Jul. 21, 1976 | [JP] | Japan | 51-87824 |
| Jul. 23, 1976 | [JP] | Japan | 51-99088 |

[51] Int. Cl.³ .................. A61B 17/12; A61B 17/28
[52] U.S. Cl. .................................... 128/321; 128/325
[58] Field of Search .......... 128/325, 346, 321, 337; 81/418, 425 R, 5.1 R; 24/259 R, 255 R, 67.9, 137 R, 81 A, 81 PE, 81 R; 29/243.56, 278, 239

[56] References Cited

U.S. PATENT DOCUMENTS

| 600,887 | 3/1898 | Pettit | 128/346 |
| 1,560,687 | 11/1925 | Hauber | 128/346 |
| 2,691,985 | 10/1954 | Newsom | 128/342 X |
| 3,344,649 | 10/1967 | Wood | 81/425 R X |
| 3,349,771 | 10/1967 | Baer | 128/325 |
| 3,827,438 | 8/1974 | Kees | 128/346 |
| 3,911,926 | 10/1975 | Peters | 128/325 |

OTHER PUBLICATIONS

Trylon Surgical Instruments Catalogue, cover page of section b and p. b15 (1971).

Primary Examiner—Robert W. Michell
Assistant Examiner—Michael H. Thaler
Attorney, Agent, or Firm—Wegner & Bretschneider

[57] ABSTRACT

A surgical clip is formed from a resilient strip piece and comprises a pair of elongated clip legs for clipping a blood vessel therebetween, and an annular bight portion connecting said clip legs at their respective one ends, said clip legs having opposed surfaces which are normally in contact with each other substantially over their whole lengths owing to the resilience of said bight portion which can be opened when the inner diameter of said annular bight portion is forcibly spread.

6 Claims, 14 Drawing Figures

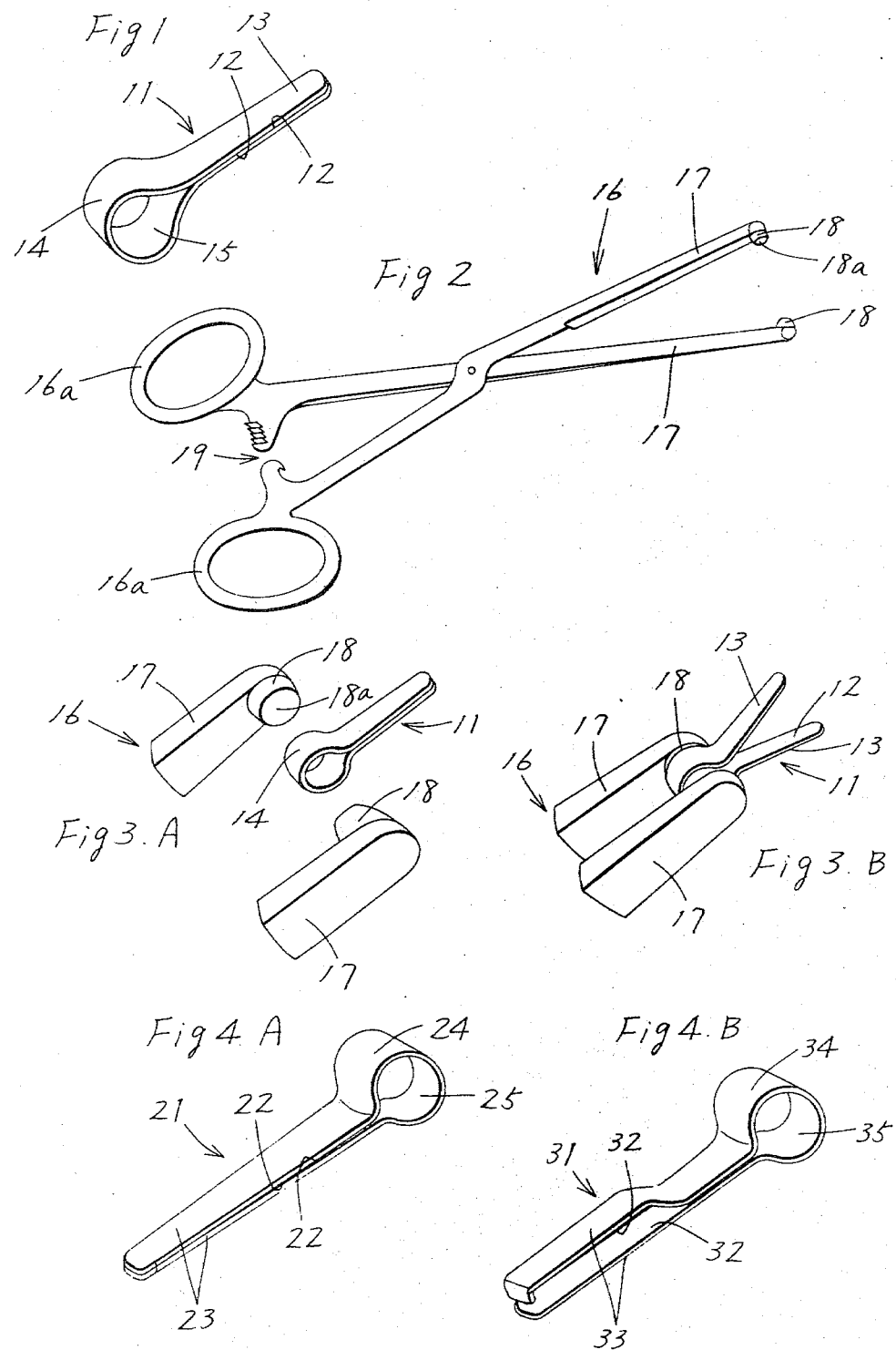

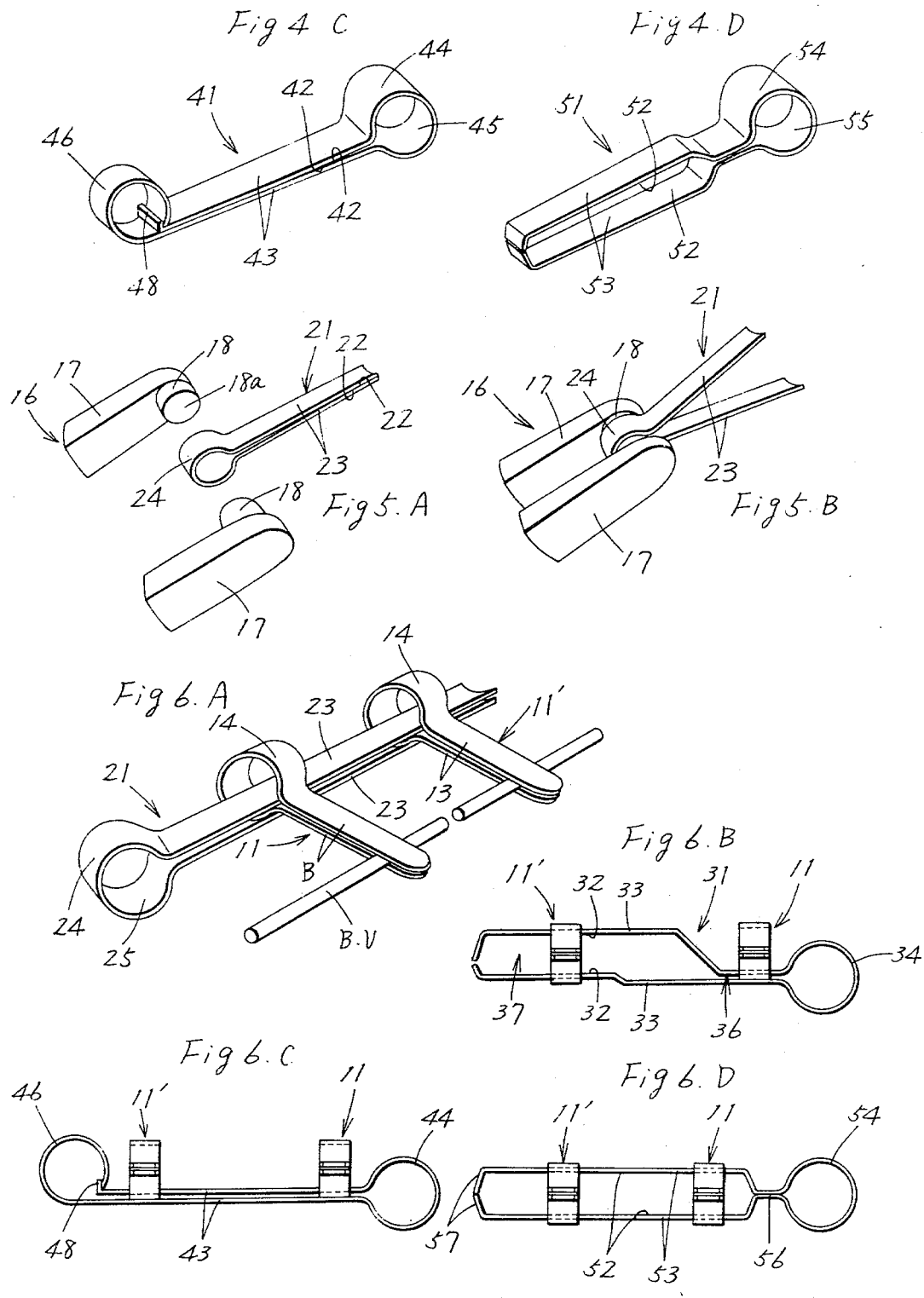

SURGICAL CLIP AND ITS ASSEMBLY

RELATED APPLICATIONS

This is a continuation-in-part of U.S. Application Ser. No. 765,742 filed Feb. 4, 1977 now abandoned.

BACKGROUND OF THE INVENTION

The present invention relates to a clip for stopping blood circulation in a surgical operation and an assembly of such clips which, when a blood vessel is cut or sewn in a surgical operation, stops the circulation of the blood in advance of the region where the cutting or sewing of the blood vessel is carried out, and it also relates to an operating device for opening and closing said clip or assembly of clips.

It is known to provide surgical clips for securely stopping the circulation of the blood by clipping a very thin blood vessel in an intricate area to be subjected to a surgical operation. Therefore, from the standpoint of performance it is desirable that such clips be simple in construction and small in size and have a sufficient gripping force to securely stop the circulation of the blood. Further, it is desirable to provide an operating forceps capable of more easily and securely operating such clips.

Conventionally, this kind of clip has been constructed wherein clip portions having a pair of opposed surfaces are connected together by separate spring means. As is apparent from its construction, this clip has the disadvantage of being complicated in construction as a whole and the spring means lacks springiness durability. Further, this known surgical clip is constructed in such a manner that the direction in which the pressing operation is effected for opening and closing the opposed clip surfaces coincides with the direction in which the opposed surfaces are opened and closed. Thus, it has the disadvantage of having the operating point shadowed by the hand when operating the clip by the conventional forceps.

On the other hand, in a surgical operation for cutting a blood vessel, the opposite sides of the place to be cut are clamped in advance by separate blood circulation stopping clips and the cutting and sewing operation are then carried out. In that case, however, it is desirable that the blood vessel be supported in a stable manner with the cut ends of the blood vessel held opposed to each other so that said ends can be brought close to each other in the subsequent sewing operation. To this end, in addition to the arrangement of the clip for clamping each cut end, it is necessary to consider a clip connecting mechanism which is useful for adjusting the relative position of the clips and supporting them in a stable condition.

A conventional assembly of two or more surgical blood circulation stopping clips connected together comprises a pair of clips each having clip portions for stopping the circulation of the blood in a blood vessel, and an operating threaded rod which connects and supports said clips in a parallel relationship, one of said clips being fixed in position with respect to the axial direction of said operating threaded rod by fixing means, the other clip being formed with a threaded opening in which said operating threaded rod is threadedly received so that it is possible to adjust the distance between said clips by rotating said operating threaded rod. With such a conventional device constructed to change the clip distance by rotation of said operating threaded rod, however, there is the disadvantage that adjustment of the clip distance results in the torque being transmitted to the clips, causing the latter to impose an excessive force on the blood vessel clamped by said clips, thereby damaging the blood vessel.

An object of the present invention is to provide an improved surgical clip having a construction adapted to substantially eliminate the disadvantages inherent in the conventional surgical clip, to provide a small surgical clip which is very simple in construction and does not need any special spring member, facilitating the handling thereof and also facilitating secondary handling including sterilization and washing, thereby improving the efficiency of surgical operation.

Another object of the invention is to provide a surgical clip constructed so that clip portions can be normally pressed against each other with a desired pressure but can be opened through a fixed angle during their operation. Thus, said clip can be brought to an area of a blood vessel where the circulation of the blood is to be stopped, so as to clip or clamp the blood vessel with a proper pressure without damaging the blood vessel, thereby improving the efficiency of surgical operation.

A further object of the invention is to provide a blood circulation stopping clip and a combination of such clips connected together by connecting means, wherein a pair of such blood circulation stopping clips are supported at a fixed position and the distance between said blood circulation stopping clips can be easily adjusted.

A still further object of the invention is to provide a connecting means capable of supporting or clamping said pair of blood circulation stopping clips in advance at a predetermined position and moving the ends of a blood vessel clamped by said pair of blood circulation stopping clips toward and away from each other by a very simple operation.

An additional object of the invention is to provide an improved forceps adapted to open and close said surgical clip and connecting clip for connecting such clips.

SUMMARY OF THE INVENTION

The surgical clip according to the invention is formed from a resilient strip piece and comprises a pair of planar legs for clipping an article therebetween and an integral means biasing the legs into pressurized contact. The clip legs have opposed surfaces which are normally in contact with each other substantially over their whole length owing to the means biasing the legs while they can be opened by insertion of a tool in an opening in the integral biasing means.

In a preferred embodiment of the invention, the integral biasing means comprises an annular bight portion integrally connected to the legs. The resilient force of the annular bight portion urges the planar legs together. The clip legs can be opened when the inner diameter of said annular bight portion is forcibly spread. Each of the clip legs is formed in an elongated tongue shape having a rounded tip portion.

A plurality of elemental clips of the above structure may be connected by an improved connection clip to form a surgical clip. The connection clip may be of a structure substantially identical to the elemental clip. Namely, the connection clip may be formed from a resilient strip piece and comprise a pair of elongated clip legs for clipping said elemental clips at their annular bight portions and an annular bight portion connecting said clip legs of said connection clip at their respective one ends. The clip legs of the connection clip have opposed surfaces which are normally urged to be in contact with each other substantially over their whole lengths owing to the resilience of said bight portion to hold said annular bight portions of said elemental clips while they can be opened to release said elemental clips when the inner diameter of said annular bight portion of said connection clip is forcibly spread. Each of the clip legs of the connection clip may preferably have widths smaller than the inner diameter of the annular bight portion of each of the elemental clips. The clip legs of the connection clip may also be provided at their free ends with lock means for preventing the leg portions from being opened.

In a preferred embodiment of the invention, the elemental clips are supported and connected by the connection clip in such a manner that one elemental clip is held at a fixed position while the other elemental clip is held so as to be slidable along the clip legs of the connection clip.

In another embodiment of the invention, the clip legs of the connection clip are insertable into the bight portions of the elemental clips and engageable with the inner peripheries of the bight portions of the elemental clips.

The forceps for opening and closing the elemental clip and the connection clip are provided with a pair of frusto-conical tips at its working ends, said frusto-conical tips having round end surfaces opposed to each other and being engageable with the bight portion of the elemental or connection clip to forcibly spread the bight portion when said forceps is closed.

DESCRIPTION OF THE DRAWINGS

Embodiments of the invention are illustrated in the drawings wherein:

FIG. 1 is a perspective view of the surgical clip according to the invention;

FIG. 2 is a forceps for opening and closing the surgical clip illustrated in FIG. 1;

FIGS. 3A and 3B are perspective views in two different states illustrating how to open the clip illustrated in FIG. 1 with the forceps illustrated in FIG. 2;

FIGS. 4A, 4B, 4C and 4D are perspective views of the connection clips illustrating four different embodiments of the invention;

FIGS. 5A and 5B are perspective views in two different states illustrating how to open the connection clip illustrated in FIG. 4A with the forceps illustrated in FIG. 2;

FIG. 6A is a perspective view of the surgical clip assembly including two elemental clips and the connection clip illustrated in FIG. 4A; and FIGS. 6B, 6C and 6D are front views of other surgical clip assemblies, including the connection clips illustrated in FIGS. 4B, 4C and 4D, respectively.

DESCRIPTION OF THE PREFERRED EMBODIMENTS

In FIG. 1, there is shown a clip 11 formed by bending a single resilient flat plate or strip piece. The clip 11 may be formed of a material, such as stainless steel, which is highly resistant to corrosion and to chemicals. The clip 11 comprises a pair of elongated planar clip legs 13 having tapered side edges and opposed surfaces 12 and an annular bight portion 14 integrally connecting said elongated clip legs at their respective one ends. Each of the clip legs 13 is formed in an elongated tongue-shape having a rounded tip portion 13. The opposed surfaces 12 are normally closed by the action of the resilience of the annular bight portion 14. The clip legs 13 are capable of opening the opposed surfaces when the inner diameter of the annular bight portion 14 is forcibly spread. In brief, the operation for opening the opposed surfaces of the clip is performed by forcibly spreading the inner diameter of the annular bight portion 14 from opposed openings 15 by some means.

The annular bight portion preferably comprises a cylindrical surface of the resilient material, the cylindrical surface substending an arc of 270°. The cylindrical surface terminates in two opposing connecting sections which curve outwardly in opposite directions and then inwardly towards each other converging at the points of connection with the planar legs.

As a preferred example of the device for this operation, a surgical clip opening and closing operating forceps 16 shown in FIG. 2 may be used in combination with the clips 11. The operating forceps 16 has a pair of frusto-conical tips 18 provided on clamp end portions 17. The frusto-conical tips 18 are attached to the forceps with their smaller round end surfaces 18a opposed to each other.

The frusto-conical tips 18 of the forceps 16 can be brought into engagement with the opposed openings 15 in the annular bight portion 14 of the clip 11 while pressing the handle portions 16a of the forceps (FIG. 3A). In this condition, the handle portions 16a of the forceps 16 is further pressed to thereby forcibly spread the inner diameter of the annular bight portion 14 of the clip 11 is thus spread, the opposed surfaces of the clip legs 13 are opened as shown in FIG. 3B against the resilient force of the annular bight portion 14. In this connection, it is to be noted that the inner diameter of the annular portion of the clip and the outer diameter of the frusto-conical tips 18 of the forceps 16 at the deepest insertion position with respect to the annular bight portion are properly preselected. More particularly, the outer diameter of the frusto-conical tips of the forceps is set at a value slightly greater than the inner diameter of the annular bight portion of the clip. The setting described above enables the opposed surfaces of the clip legs 13 of the clip 11 to be opened by a fixed angle at a point where the smaller round end surfaces of the frusto-conical tips contact each other whenever the frusto-conical tips of the forceps are inserted into the annular bight portion of the fullest extent. With the opposed surfaces of the clip legs of the clip thus opened, the blood vessel is then positioned between said opposed surfaces. The pressure on the handle portions 16a of the forceps 16 is then removed to allow the clip legs of the clip to return to their normal condition under the action of the elastic or resilient force of the annular bight portion so as to securely clip the blood vessel positioned therebetween, thereby stopping the circulation of the blood. The forceps 16 may be provided with hook means 19 on its handle portions for the purpose of maintaining the forceps in its condition holding the clip between its frusto-conical tips.

As described above, since said clip is constructed by bending a single flat elastic plate, it is provided as a clip very simple in construction and small in size in that it does not require a spring member of special complicated construction. Therefore, it can be said that it is easy to handle and superior in secondary handling including sterilization and washing. Further, since it is designed so that its clamp surfaces are normally pressed against each other with a constant pressure, it is possible to stop the circulation of the blood in a blood vessel in a secure and stable manner.

On the other hand, the forceps for opening and closing said clip is of a construction such that it is provided with a pair of frusto-conical tips engageable with the inner diameter of the annular bight portion of the clip from opposite sides of said annular bight portion. Further, according to the invention, said clip is used in such a manner that it is held by being locked by the frusto-conical tips of said forceps and brought to an area of the body to be operated. Therefore, even when said area is observed by a microscope or the like, there is no possibility of being shaded by the hand, thus allowing the area to be observed in an optimum condition. In this respect also, the invention can be said to improve the efficiency of surgical operation.

A plurality of clips of the above-described structure may be connected by a connection clip to form a clip assembly. The connection clip may be formed in a shape similar to the elemental clip described in the above.

Connection clips according to some preferred embodiments of the invention are shown in FIGS. 4A, 4B, 4C and 4D. These connecting clips are indicated by the reference numerals 21, 31, 41 and 51 for convenience. Each of the connecting clips 21, 31, 41 and 51 is formed by bending a single resilient flat plate member or strip piece. Preferably, it may be formed of a flat plate member of a material highly resistant to corrosion and to chemical, such as stainless steel. The connecting clips 21, 31, 41 and 51 comprise elongated clip legs 23, 33, 43 and 53, having opposed surfaces 22, 32, 42 and 52 opposed to each other and annular bight portions 24, 34, 44 and 54 which integrally connect said clip legs, respectively. The elongated clip legs can be formed to have slightly tapered side edges and they are normally urged against each other by the action of the resilience of the annular bight portion 24, 34, 44 and 54.

The clip legs can be operated to be open by means for forcibly spreading the inner diameter of the annular bight portion. As for the means for opening the opposed strips, a forceps used in the operation for opening and closing the clip previously described with reference to FIGS. 2, 3A and 3B can be used as a combination tool. The procedure in operating the connecting clip 21 by using the forceps illustrated in FIG. 2 is illustrated in FIGS. 5A and 5B. The frusto-conical tips on the grip side of the forceps 16 are brought into engagement with the opposed openings 25 in the annular bight portion 24 of the connecting clip 21 while pressing the handle portion of the forceps. In this condition, the handle portion of the forceps 16 is further pressed to thereby forcibly spread the inner diameter of the annular bight portion 24 of the connection clip. As the inner diameter of the annular bight portion of the connection clip 21 is thus spread, the opposed surfaces of said clip legs are opened against the elastic or resilient force of the annular bight portion 24. In this connection, it is to be noted that the inner diameter of the annular bight portion of said clip 21 and the outer diameter of the frusto-conical tips 18 of said forceps 16 at the deepest insertion position with respect to the annular bight portion are properly pre-selected. More particularly, the outer diameter of the frusto-conical tips of the forceps 16, corresponding to the base of the frusto-conical tips, is set at a value slightly greater than the inner diameter of the annular bight portion 24 of the clip 21 whereas the top of the frusto-conical tip has a diameter smaller than the inner diameter of the annular bight portion of the clip. The setting described above enables the opposed surfaces of the clip legs of the clip to be opened by a fixed amount at a point where the smaller round end surfaces 18a of the frusto-conical tips 18 contact each other whenever the frusto-conical tips 18 of the forceps 16 are inserted into said annular bight portion 24 to the fullest extent.

Alternatively, the height of the frusto-conical tip 18 is also pre-selected with respect to the height of the cylindrical surface of the annular bight portion 24. If the cylindrical surface height is two times the height of the frusto-conical tip 18, or more, the clip will be prevented from rotating as the frusto-conical tips will not touch and the cylinder will be grasped by the forceps.

The connection clips illustrated in FIGS. 4B, 4C and 4D may also be opened by using the forceps illustrated in FIG. 2 in the same manner as described in the above.

The connecting clips 21, 31, 41 and 51 are used to connect at least two elemental clips 11 previously described referring to FIG. 1. The clip legs 22, 32, 42 and 52 have a sufficient length necessary to receive such unit clips arranged side by side.

The connecting clip 21 shown in FIG. 4A is similar in shape to the previously described surgical elemental clip 11 but is different therefrom in that it has longer clip legs 22. The connecting clip 22 shown in FIG. 4A has a construction such that the opposed surfaces 22 are normally contacted with each other over the entire area thereof by the action of the resilience of the annular bight portion 24. The construction of the clip legs of the connecting clip 21 in this example is such that their contact surfaces, when seen in a cross-sectional view, are curved and are contacted with each other with said curved surfaces being placed one upon the other.

FIG. 6A illustrates a clip assembly used for surgical operation. As is clear from FIG. 6, the connection clip 21 clamps at its clip legs 23 the annular bight portions 14 of a pair of blood circulation stopping clips 11 which, in turn, clamp the opposite sides of a place of a blood vessel to be cut, and supports said blood circulation stopping clips in juxtaposed position. Therefore, the width of the clamp portions 23 of the connection clip 21 is slightly smaller than the inner diameter of the annular bight portion 14 of the blood circulation stopping clip 11. The curvature of the clamp portions of the connection clip 21 is equal or approximately equal to that of the annular bight portion of the blood circulation clips 11. In this way, a pair of blood circulation stopping clips are securely supported by a single connection clip 21. According to this example of use, a pair of blood circulation stopping clips supported by connection clips are positioned on the opposite sides of a place of a blood vessel to be cut in a surgical operation, and then the blood vessel is cut and is sewn while suitably adjusting the distance between said blood circulation stopping clips controlled by the connection clip.

Another clip assembly including the connection clip 31 shown in FIG. 4B is shown in FIG. 6B. The connection clip 31 supports a pair of blood circulation stopping clips 11 in such a manner that it clamps the annular bight portion 14 of one blood circulation clip 11 as in the case of the first example, while it internally holds the inner diameter of the annular bight portion of the other blood circulation clip 11'. Thus, the connection clip 31 in this example comprises including a clip section 36 normally contacted with each other with opposed surfaces cooperating with each other to clamp a part of the annular bight portion 14 of the blood circulation stopping clip, and a support section 37 for internally supporting the inner diameter of the annular bight portion 14 of the blood circulation stopping clip 11. In the assembly illustrated in FIG. 6B, the blood circulation stopping clip 11 is fixedly held at the clip section 36 while the other blood circulation stopping clip 11' with its inner diameter internally supported can slide in a direction of the length of the connection clip 31. Therefore, the distance between the cut ends of the blood vessel controlled by said pair of blood circulation stopping lips 11, 11' can be adjusted without any difficulty, enabling the sewing of the blood vessel to be performed with the cut ends contacting each other.

The connection clip 41 shown in FIG. 4C is substantially similar in construction to the connection clip 31 in the first embodiment of FIG. 4A except that it has locking means 46 at the free ends of a pair of clip legs 42 to prevent the opening of said free ends. More particularly, the locking means 46 comprises a curved strip 47 integrally formed at the free end of one leg and a projection 48 at the free end of the other leg adapted to arrest the front end of said curved strip. According to this embodiment, the forceps 16 may also be used as means for unlocking said locking means 46. More particularly, by inserting the frusto-conical tips 18 of the forceps 16 into the annular bight portion formed by the curved strip 47 of the locking means, the locking action on the free ends of the clamp strips is removed.

The connection clip 51 is shown in FIG. 4D is designed to support a pair of blood circulation stopping clips 11, 11' internally at the inner diameters of their annular bight portions 14, 14' (see FIG. 6D). The connection clip 51 has a clamp section 53 constructed in such a manner that normally it is capable of internally supporting the inner diameters of the annular bight portions of said blood circulation stopping clips 11, 11' over the entire length of the clamp section. The connection clip 51 is constructed so that connecting section 56 extending from its annular bight portion 54 and the free ends 57 on the clamp section side are bent toward each other and bear against each other.

As has been described so far, according to the surgical slip of the present invention, a pair of blood circulation stopping clips for clamping the opposite sides of a place of a blood vessel to be cut can be supported at fixed positions and the distance between said blood circulating clips can be adjusted according to the surgical operation without any difficulty, thereby improving the efficiency of surgical operation. Further, by suitably designing a pair of blood circulation stopping clips, the connection clip for connecting such pair of blood circulation stopping clips and the forceps for operating the same, they are cooperatively combined to provide a set of tools for surgical operation, and in this respect also it is possible to improve the efficiency of surgical operation.

What is claimed is:

1. A blood circulation stopping clip assembly comprising a plurality of elemental blood circulation stopping clips each elemental clip being formed of a resilient strip piece and comprising a pair of elongated clip legs for clipping a blood vessel therebetween and an annular bight portion connecting said clip legs at their respective one ends, each of said clip legs being formed in an elongated tongue shape having tapered side edges each of said clip legs having opposed surfaces which are normally urged to be in contact with each other substantially over their whole areas owing to the resilience of said bight portion and can be opened when the inner diameter of said annular bight portions forcibly spread; and a connection clip for supporting and connecting said plurality of elemental clips in parallel and in a spaced relationship, said connection clip being formed of a resilient strip piece and comprising a pair of elongated clip legs for clipping said elemental clips at their annular bight portions and an annular bight portion connecting said clip legs of said connection clip at their respective one ends, said clip legs of said connection clip having opposed surfaces which are normally urged to be in contact with each other owing to the resilience of said bight portion to hold said annular bight portions of said elemental clips while they can be opened to release said elemental clips when the inner diameter of said annular bight portion of said connection clip is forcibly spread.

2. A blood circulation stopping clip assembly as defined in claim 1, in which each said clip legs of said connection clip has a width smaller than the inner diameter of said annular bight portion of each of said elemental clips.

3. A blood circulation stopping clip assembly as defined in claim 1, in which said clip legs of said connection clip provided at their free ends with lock means for preventing said leg portions from being opened.

4. A blood circulation stopping clip assembly as defined in claim 1, in which said elemental clips are supported and connected by said connection clip in such a manner that one elemental clip is held at a fixed portion while the other elemental clip is held so as to be slidable along said clip legs of said connection clip.

5. A blood circulation stopping clip assembly as defined in claim 1, in which said clip legs of said connection clip are insertable into said bight portions of said elemental clips and engageable with the inner peripheries of said bight portions of said elemental clips.

6. A combination of a blood circulation stopping clip and a forceps for opening and closing said clip in which said blood circulation stopping clip is formed of a resilient strip piece and comprises a pair of elongated clip legs for clipping a blood vessel therebetween and an annular bight portion connecting said clip legs at their respective one ends, each of said clip legs being formed in an elongated tongue shape having tapered side edges, each of said clip legs having opposed surfaces which are normally urged to be in contact with each other substantially over their whole area owing to the resilience of said bight portion which can be opened when the inner diameter of said bight portion is forcibly spread and said forceps for opening and closing said clip is provided with a pair of frusto-conical tips at its working ends, said frusto-conical tips having round end surfaces opposed to each other and being engageable with said bight portion of said clip to forcibly spread said bight portion when said forceps is closed, the outer diameter of the frusto-conical tips of said forceps being slightly greater than the inner diameter of the annular bight portion of said blood circulation clip so that the opposed surfaces of said clip legs of said clip may be opened by a fixed angle at a point where the smaller round end surfaces of the frusto-conical tips contact each other whenever the frusto-conical tips of said forceps are inserted into said annular bight portion to the fullest extent.

* * * * *